United States Patent [19]

Feld et al.

[11] Patent Number: 4,714,605

[45] Date of Patent: Dec. 22, 1987

[54] TECHNETIUM-99M LABELED DIOXIME COMPLEXES

[75] Inventors: Thomas A. Feld, Califon; Pedro N. Juri, Lawrenceville, both of N.J.; Elizabeth N. Treher, Washington Crossing, Pa.

[73] Assignee: E. R. Squibb & Sons, Inc., Princeton, N.J.

[21] Appl. No.: 918,434

[22] Filed: Oct. 14, 1986

[51] Int. Cl.$^4$ .................... A61K 43/00; C07F 13/00
[52] U.S. Cl. ...................... 424/1.1; 534/14; 564/258; 564/267; 564/268
[58] Field of Search ............. 424/1.1; 534/10, 14; 564/258, 267, 268

[56] References Cited

PUBLICATIONS

Boston et al., "Encapsulation Reaction. Synthesis of the Clathro Chelate 1,8-Bis(fluoroboro)-2,7,9,14,15,-20-hexaoxa-3,6,10,13,16,19-hexaaza-4,5,11,12,17,-18-hexamethylbicyclo[6.6.6]eicosa-3,5,10,12,16,-18-hexaenecobalt(III) ion", J.A.C.S., 90:6859-6860, (1968).

Boston et al., "Encapsulation Reactions. Synthesis and Study of Clathro Chelates Derived from Dimethylglyoxime, Cobalt, and Lewis Acids", J.A.C.S., 95(13):4163 (1973).

Simek, "Herstellung Von Kalium-Und Natriumdimethylglyoximatoniccolat(IV)", Collection Czechoslov. Chem. Comm., 27:220 (1962).

Robbins et al., "Synthesis and Electrochemistry of Iron-(II)Clathrochelates", Inorg. Chem., 24(21):3381 (1985).

*Primary Examiner*—John F. Terapane
*Assistant Examiner*—M. L. Mallon
*Attorney, Agent, or Firm*—Lawrence S. Levinson; Donald J. Barrack

[57] ABSTRACT

Technetium-99m labeled dioxime complexes are useful for imaging the myocardium, brain and hepatobiliary system, in humans and other mammalian species.

12 Claims, No Drawings

TECHNETIUM-99M LABELED DIOXIME COMPLEXES

BRIEF DESCRIPTION OF THE INVENTION

Technetium-99m labeled dioxime complexes having the formula

are useful as imaging agents in humans and other mammalian species. In formula I, and throughout the specification, the symbols are as defined below.

X is a halogen;
Y is a vicinal dioxime having the formula

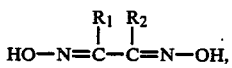

or a pharmaceutically acceptable salt thereof, and $R_1$ and $R_2$ are each independently hydrogen, halogen, alkyl, aryl, amino or a 5 or 6-membered nitrogen or oxygen containing heterocycle, or together $R_1$ and $R_2$ are —$(CR_3R_4)_n$— wherein n is 3, 4, 5 or 6 and $R_3$ and $R_4$ are each independently hydrogen or alkyl.

Listed below are definitions of the terms used to describe the complexes of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups.

The terms "halo" and "halogen" refer to fluorine, chlorine, bromine and iodine.

The expression "5 or 6-membered nitrogen or oxygen containing heterocycle" refers to 5 and 6-membered rings containing at least one nitrogen or oxygen atom. Exemplary aliphatic groups are 1,4-dioxanyl, furanyl and dehydro derivatives of a compound having the formula

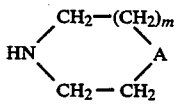

wherein m is 0 or 1 and A is O, N–$R_6$ or CH–$R_6$ wherein $R_6$ is hydrogen, alkyl, aryl or arylalkyl. Such groups include pyrrolidinyl, piperidinyl, morpholinyl, piperazinyl, 4-alkyl-piperazinyl, 4-alkylpiperidinyl, and 3-alkylpyrrolidinyl groups. Also included within the expression "5 or 6-membered nitrogen or oxygen containing heterocycle" are aromatic groups. Exemplary aromatic groups are pyrrolyl, imidazolyl, oxazolyl, pyrazolyl, pyridinyl, and pyrimidinyl groups. The above groups can be linked via a hetero atom or a carbon atom.

DETAILED DESCRIPTION OF THE INVENTION

Preparation of the complexes of this invention can best be accomplished using technetium-99m in the form of the pertechnetate ion. The pertechnetate ion can be obtained from commercially available technetium-99m parent-daughter generators; such technetium is in the +7 oxidation state. The generation of the pertechnetate ion using this type of generator is well known in the art, and is described in more detail in U.S. Pat. No. 3,369,121 and 3,920,995. These generators are usually eluted with saline solution and the pertechnetate ion is obtained as the sodium salt.

The technetium-99m labeled complexes of this invention can be prepared by first combining pertechnetate ion (in the form of a salt) with a vicinal dioxime of formula II and a halogen. This can be accomplished by mixing a vicinal dioxime of formula II, a source of halogen and a stabilizing agent. The dioxime should preferably be present in a concentration of about 9 to 43 millimolar. The source of halogen (X) can be an acid or salt which dissociates to release the appropriate halogen. Chlorine is the most preferred halogen. It has been found that the halogen should be present in the reaction mixture in a concentration of about 0.15 to 4.5 molar. The stabilizing agent should be present in a concentration of about 0.008 to 0.04 millimolar. The reaction mixture should also contain a reducing agent capable of reducing pertechnetate ion. Stannous ion is the preferred reducing agent, and can be introduced in the form of a stannous salt such as a stannous halide (e.g., stannous chloride or stannous fluoride). The reducing agent will, preferably be present in a concentration of about 1.5 micromolar to 6.6 millimolar. The formation of the complex proceeds readily if its components are combined and left undisturbed for about 1 to 60 minutes at room temperature. Alternatively, the components can be mixed for about 1 to 30 minutes, e.g., by shaking or sonication.

The stabilizing agent is a substance which is present during the preparation of the complex of this invention to prevent or retard an unwanted alteration of the physical state of the complex and to increase the radiochemical purity of the labeled product. The stabilizing agent can be a primary, secondary or tertiary amine, (e.g., mono-, di- or trialkylamines, arylamines, arylalkylamines, etc.), an amino alcohol, (e.g., alkanolamines), a diamine (e.g., alkanediamines), an amino acid or ester thereof (e.g., glycine or an alkyl ester thereof), or a salt of any of the above compounds, or α-, β- or γ-cyclodextrin.

Complexing agents (also known in the art as chelating agents) and/or accelerators (also known in the art as catalysts) can be included as part of the complexing reaction. These components should be pharmaceutically acceptable, as should all of the components of the products of this invention.

Exemplary complexing agents are diethylenetriamine-pentaacetic acid (DTPA), ethylene glycolbis(β-aminoethyl ether)-N,N'-tetraacetic acid (EGTA), ethylenediamine tetraacetic acid (EDTA), citric acid, tartaric acid, malonic acid, etc.

An accelerator (catalyst) serves to improve the radiochemical purity (i.e., percent of the radioactivity that is in the desired chemical form) of the product. Exemplary accelerators are the α-hydroxycarboxylic acids such as citric acid, tartaric acid, and malonic acid.

The structure of complexes of this invention has been investigated and is believed to be:

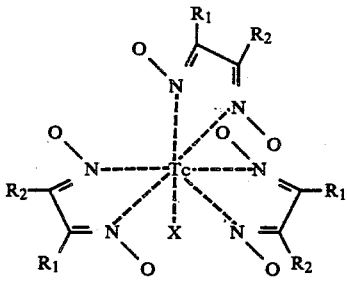

Because of the short half-life of technetium-99m (i.e., 6.02 hours), it is necessary to prepare the complexes of this invention at, or near, the site where they are to be used. A kit having all of the components, other than the pertechnetate ion, needed to prepare the technetium-99m dioxime complexes of formula I is an integral part of this invention. Such a kit contains a source of a halogen, a dioxime of formula II, or a pharmaceutically acceptable salt thereof, a stabilizing agent and a reducing agent. It may optionally contain a complexing agent and/or accelerator.

The complexes of this invention are useful as imaging agents. More specifically, they are useful for imaging the myocardium, brain and the hepatobiliary system in humans and other mammlian hosts.

The complexes of this invention can be administered to a host by bolus intravenous injection. The size of the host, and the imaging system used, will determine the quantity of radioactivity needed to produce diagnostic images. For a human host, the quantity of radioactivity injected will normally range from about 5 to 20 millicuries of technetium-99m.

The following examples are specific embodiments of this invention.

EXAMPLE 1

$^{99m}$Tc (chloro)(1,2-cyclohexanedione dioxime)$_3$

Method I

Into a 10 ml siliconized serum vial were measured 2.0 mg of 1,2-cyclohexanedione dioxime, 50 mg of γ-cyclodextrin, 100 mg of sodium chloride, 10 mg of citric acid and 50 μg of anhydrous stannous chloride in 1 μl of concentrated hydrochloric acid.

Sodium pertechnetate* in physiological saline (0.1 ml) was added to the vial, the vial was swirled briefly, and after standing at room temperature for 5 minutes the yield** of $^{99m}$Tc (chloro)(1,2-cyclohexanedione dioxime)$_3$ was 54% as determined by HPLC (high pressure liquid chromatography).

Method II

Into a 10 ml siliconized serum vial were measured 2.0 mg of 1,2-cyclohexanedione dioxime, 15 mg of citric acid (0.15 ml of a 10 mg/ml aqueous solution), 3 mg of diethylenetriamine pentaacetic acid, 10 mg of ethanolamine hydrochloride, 100 mg of sodium chloride, 0.2 ml of water and approximately 50 μg of anhydrous stannous chloride in 1 μl of concentrated hydrochloric acid.

Sodium pertechnetate in physiological saline (0.1 ml) was added to the vial which was swirled briefly and then left undisturbed at room temperature for 15 minutes yielding 35% of $^{99m}$Tc (chloro)(1,2-cyclohexanedione dioxime)$_3$ as determined by HPLC.

*The sodium pertechnetate used in these examples was obtained by eluting a sterile technetium-99m generator with physiological saline.
**As used in these examples, the yield was determined by HPLC and is reported as the percent of radioactivity eluted in the desired form.

EXAMPLE 2

$^{99m}$Tc (bromo)(1,2-cyclohexanedione dioxime)$_3$

Following the procedure of Example 1, Method I, but substituting 100 mg of potassium bromide for sodium chloride, yielded 59% of $^{99m}$Tc (bromo)(1,2-cyclohexanedione dioxime)$_3$.

EXAMPLE 3

$^{99m}$Tc (iodo)(1,2-cyclohexanedione dioxime)$_3$

Following the procedure of Example 1, Method I, but substituting 100 mg of sodium iodide for sodium chloride, yielded 11% of $^{99m}$Tc (iodo)(1,2-cyclohexanedione dioxime)$_3$.

EXAMPLE 4

$^{99m}$Tc (fluoro)(1,2-cyclohexanedione dioxime)$_3$

Following the procedure of Example 1, Method I, but substituting 100 mg of sodium fluoride for sodium chloride, yielded 23% of $^{99m}$Tc (fluoro)-(1,2-cyclohexanedione dioxime)$_3$.

EXAMPLE 5

$^{99m}$Tc (chloro)(3-methyl-1,2-cyclopentanedione dioxime)$_3$

Following the procedure of Example 1, Method I, but substituting 2.0 g of 3-methyl-1,2-cyclopentanedione dioxime for 1,2-cyclohexanedione dioxime, and using 0.2 ml of sodium pertechnetate in physiological saline, yielded 48% of $^{99m}$Tc (chloro)-(3-methyl-1,2-cyclopentanedione dioxime)$_3$.

EXAMPLE 6

$^{99m}$Tc (chloro)(1,2-cycloheptanedione dioxime)$_3$

Following the procedure of Example 1, Method I, but substituting 2.0 mg of 1,2-cycloheptanedione dioxime for 1,2-cyclohexanedione dioxime, and using 0.2 ml of sodium pertechnetate in physiological saline, yielded 80% of $^{99m}$Tc (chloro)-(1,2-cycloheptanedione dioxime)$_3$.

EXAMPLE 7

$^{99m}$Tc (bromo)(1,2-cycloheptanedione dioxime)$_3$

Following the procedure of Example 1, Method I, but substituting 2.0 mg of 1,2-cycloheptanedione dioxime for 1,2-cyclohexanedione dioxime and 100 mg of potassium bromide for stannous chloride, and using 0.2 ml of sodium pertechnetate in physiological saline, yielded 55% of $^{99m}$Tc (bromo)-(1,2-cycloheptanedione dioxime)$_3$.

EXAMPLE 8

$^{99m}$Tc (fluoro)(1,2-cycloheptanedione dioxime)$_3$

Following the procedure of Example 1, Method I, but substituting 2.0 mg of 1,2-cycloheptanedione dioxime for 1,2-cyclohexanedione dioxime and 100 mg of sodium fluoride for sodium chloride, and using 0.2 ml of sodium pertechnetate in physiological saline, yielded 80% of $^{99m}$Tc (fluoro)(1,2-cycloheptanedione dioxime)$_3$.

EXAMPLE 9

$^{99m}$Tc (iodo)(1,2-cycloheptanedione dioxime)$_3$

Following the procedure of Example 1, Method I, but substituting 2.0 mg of 1,2-cycloheptanedione dioxime for 1,2-cyclohexanedione dioxime and 100 mg of sodium iodide for sodium chloride, and using 0.2 ml of sodium pertechnetate in physiological saline, yielded 3% of $^{99m}$Tc (iodo)(1,2-cycloheptanedione dioxime)$_3$.

EXAMPLE 10

$^{99m}$Tc (fluoro)(1,2-cyclooctanedione dioxime)$_3$

Following the procedure of Example 1, Method I, but substituting 2.0 mg of 1,2-cyclooctanedione dioxime for 1,2-cyclohexanedione dioxime and 100 mg of sodium fluoride for sodium chloride, and using 0.2 ml of sodium pertechnetate in physiological saline, yielded 19% of $^{99m}$Tc (fluoro)(1,2-cyclooctanedione dioxime)$_3$.

EXAMPLE 11

$^{99m}$Tc (chloro)(2,3-butanedione dioxime)$_3$

Method I

Following the procedure of Example 1, Method I, but substituting 2.0 mg of 2,3-butanedione dioxime for 1,2-cyclohexanedione dioxime, and using 0.2 ml of sodium pertechnetate in physiological saline, yielded 15% of $^{99m}$Tc (chloro)-(2,3-butanedione dioxime)$_3$.

Method II

Into a 10 ml siliconized serum vial were measured 2.0 mg of 2,3-butanedione dioxime (0.2 ml of a 10 mg/ml ethanol solution), 15 mg of citric acid (0.15 ml of a 100 mg/ml aqueous solution), 3 mg of diethylenetriamine pentaacetic acid, 10 mg of diisopropylamine hydrochloride, 100 mg of sodium chloride, 0.2 ml of water and 50 μg of anhydrous stannous chloride in 1 μl of concentrated hydrochloric acid.

Sodium pertechnetate in physiological saline (0.1 ml) was added to the vial which was shaken and left undisturbed at room temperature for 10 minutes yielding 40% of $^{99m}$Tc (chloro)(2,3-butanedione dioxime)$_3$ as determined by HPLC.

Method III

Into a 10 ml siliconized serum vial were measured 2.0 mg of 2,3-butanedione dioxime, 50 mg of γ-cyclodextrin, 100 mg of sodium chloride, 10 mg of citric acid and 50 μl of stannous pyrophosphate (saturated aqueous solution).

Sodium pertechnetate in physiological saline (0.1 ml) was added and the mixture was sonicated at room temperature for 15 minutes yielding 61% of $^{99m}$Tc(chloro)(2,3-butanedione dioxime)$_3$ as determined by HPLC.

The compound of Example 11 was also prepared using the procedure of Example 11, Method II, but substituting the following stabilizers for diisopropylamine hydrochloride: ammonium chloride, hexamethylene tetraamine, piperidine hydrobromide, pyridine hydrochloride, tetraethylammonium bromide, triethylamine hydrochloride, 1,3-propanediamine hydrochloride, aniline hydrochloride, phenethylamine hydrochloride, ethanolamine hydrochloride, glycine hydrochloride, glycine methyl ester hydrochloride, and 6-aminocaproic acid.

What is claimed is:

1. A technetium-99m dioxime complex having the formula

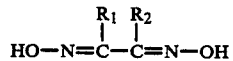

wherein
X is a halogen; and
Y is a vicinal dioxime having the formula $$\overset{R_1}{\underset{|}{\phantom{H}}}\overset{R_2}{\underset{|}{\phantom{H}}}$$
$$HO-N=C-C=N-OH$$

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are $-(CR_3R_4)_n-$ wherein n is 3, 4, 5 or 6 and $R_3$ and $R_4$ are each independently hydrogen or alkyl.

2. A technetium-99m dioxime complex in accordance with claim 1, wherein X is chlorine or bromine.

3. A technetium-99m dioxime complex in accordance with claim 1, wherein X is chlorine.

4. A technetium-99m dioxime complex in accordance with claim 1, wherein Y is 1,2-cyclohexanedione dioxime, 2,3-butanedione dioxime, 3-methyl-1,2-cyclopentanedione dioxime, 1,2-cycloheptanedione dioxime, or 1,2-cyclooctanedione dioxime.

5. A technetium-99m dioxime complex in accordance with claim 1, wherein Y is 1,2-cyclohexanedione dioxime.

6. A technetium-99m dioxime complex in accordance with claim 1, wherein Y is 2,3-butanedione dioxime.

7. A technetium-99m dioxime complex in accordance with claim 1, wherein Y is 3-methyl-1,2-cyclopentanedione dioxime.

8. A technetium-99m dioxime complex in accordance with claim 1, wherein Y is 1,2-cycloheptanedione dioxime.

9. A technetium-99m dioxime complex in accordance with claim 1, wherein Y is 1,2-cyclooctanedione dioxime.

10. A kit suitable for labeling with technetium-99m, said kit comprising:
 (i) a source of a halogen;
 (ii) a dioxime having the formula

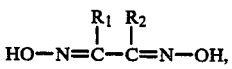

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are $-(CR_3R_4)_n-$ wherein n is 3, 4, 5 or 6 and $R_3$ and $R_4$ are each independently hydrogen or alkyl;
 (iii) a stabilizing agent; and
 (iv) a reducing agent.

11. A kit in accordance with claim 10, wherein the source of halogen is a source of chlorine or bromine.

12. A kit in accordance with claim 11 wherein the dioxime is 1,2-cyclohexanedione dioxime, 2,3-butanedione dioxime, 3-methyl-1,2-cyclopentanedione dioxime, 1,2-cycloheptanedione dioxime, or 1,2-cyclooctanedione dioxime.

* * * * *